(12) United States Patent
Gaitonde et al.

(10) Patent No.: US 8,530,488 B2
(45) Date of Patent: Sep. 10, 2013

(54) CRYSTALLINE FORMS OF BOSENTAN

(75) Inventors: Abhay Gaitonde, Maharashtra (IN); Bindu Manojkumar, Maharashtra (IN); Sandeep Mekde, Maharashtra (IN); Prakash Bansode, Maharashtra (IN); Dattatraya Shinde, Maharashtra (IN); Sunanda Phadtare, Maharashtra (IN)

(73) Assignee: Generics [UK] Limited, Hertfordshire (GB)

( * ) Notice: Subject to any disclaimer, the term of this patent is extended or adjusted under 35 U.S.C. 154(b) by 54 days.

(21) Appl. No.: 12/739,303

(22) PCT Filed: Oct. 24, 2008

(86) PCT No.: PCT/GB2008/050986
§ 371 (c)(1),
(2), (4) Date: Sep. 10, 2010

(87) PCT Pub. No.: WO2009/053748
PCT Pub. Date: Apr. 30, 2009

(65) Prior Publication Data
US 2010/0331352 A1 Dec. 30, 2010

(30) Foreign Application Priority Data
Oct. 24, 2007 (IN) .......................... 2108/MUM/2007

(51) Int. Cl.
*A01N 43/54* (2006.01)
*A61K 31/505* (2006.01)

(52) U.S. Cl.
USPC .......................................... 514/269; 544/296

(58) Field of Classification Search
USPC .......................................................... 544/296
See application file for complete search history.

(56) References Cited

U.S. PATENT DOCUMENTS

| | | | |
|---|---|---|---|
| 5,292,740 A | 3/1994 | Burri et al. | |
| 5,739,333 A | 4/1998 | Yamada et al. | |
| 6,136,971 A | 10/2000 | Harrington et al. | |
| 6,479,692 B1 | 11/2002 | Ekwuribe et al. | |
| 8,288,401 B2 * | 10/2012 | Gaitonde et al. | 514/269 |
| 2008/0188663 A1 * | 8/2008 | Kumar et al. | 546/114 |
| 2008/0242687 A1 | 10/2008 | Gant et al. | |
| 2009/0156811 A1 | 6/2009 | Taddei et al. | |
| 2009/0291974 A1 | 11/2009 | Zhu | |
| 2010/0331352 A1 * | 12/2010 | Gaitonde | 514/269 |
| 2011/0014291 A1 * | 1/2011 | Dixit et al. | 424/489 |
| 2012/0041200 A1 | 2/2012 | Biffi et al. | |

FOREIGN PATENT DOCUMENTS

| | | |
|---|---|---|
| CA | 2 071 193 | 5/1992 |
| CN | 1425007 | 6/2003 |
| EP | 0 526 708 | 2/1993 |
| EP | 0 526 708 B1 | 2/1993 |
| EP | 0 743 307 A | 9/2001 |
| EP | 0 743 307 B1 | 9/2001 |
| EP | 2 072 503 | 6/2009 |
| IN | 1245/MUM/2007 | 6/2007 |
| WO | WO 01/36384 | 5/2001 |
| WO | WO 01/43742 | 6/2001 |
| WO | WO 01/55120 | 8/2001 |
| WO | WO 0155120 A1 * | 8/2001 |
| WO | WO 2004/076443 | 9/2004 |
| WO | WO 2004/081016 | 9/2004 |
| WO | WO 2004/087660 | 10/2004 |
| WO | WO 2008/135795 | 11/2008 |
| WO | WO 2009/004374 | 1/2009 |
| WO | WO 2009/047637 | 4/2009 |
| WO | WO 2009/093127 | 7/2009 |
| WO | WO 2009/095933 | 8/2009 |
| WO | WO 2009/098517 | 8/2009 |
| WO | WO 2009/112954 | 9/2009 |
| WO | WO 2010/061210 | 6/2010 |

OTHER PUBLICATIONS

S.L. Morissette et al., Advanced Drug Delivery Reviews, 56, 275-300 (2004).*
S.R. Vippagunta et al., Advanced Drug Delivery Reviews, 48, 3-26 (2001).*
J.K. Guillory, Generation of Polymorphs, Hydrates, Solvates, and Amorphous Solids, in Polymorphism in Pharmaceutical Solids 183-220 (H.G. Brittain ed., 1999).*
Harrington Peter J. et al., "Research and Development of a Second Generation Process for Bosentan", Organic Process Research and Development, Cambridge, GB, vol. 6, Jan. 1, 2002, pp. 120-124.
Harada Hironori et al., "Ethenesulfonamide and Ethanesulfonamide Derivatives, a Novel Class of Orally Active Endothelin-A Receptor Antagonists", Bioorganic & Medicinal Chemistry, Elsevier Science Ltd., GB, vol. 9, Jan. 1, 2001, pp. 2955-2968.
Neidhart W. et al., "The Discovery of Nonpeptide Endothelin Receptor Antagonists. Progression Towards Bosentan", Chimia, AARAU, CH, vol. 50, Jan. 1, 1996, pp. 519-524.
Yang Ning et al., "Synthesis of Bosentan as an Endothelin Receptor Antagonist", Zhongguo Yaowu Huaxue Zazhi—Chinese Journal of Medicinal Chemistry, GAI-KAI Bianjibu, Shenyang, CN, vol. 15, No. 4, Jan. 1, 2005, pp. 230-223.
International Search Report PCT/GB2008/050986 dated Apr. 28, 2009 (7 pgs.).
Background Information for the Oct. 2002 ACPS Meeting. Scientific Considerations of Polymorphism in Pharmaceutical Solids: Abbreviated New Drug Applications.
Bosentan Wikipedia extract Jun. 26, 2008.
C. Boss et al., Bioorganic Medicinal Chemistry Letters, 13, 951-954 (2003).
Chemblink webpage re 4,6-dichloro-5-(2-methoxyphenoxy)-2,2'-bipyrimidine Jan. 19, 2009.
Chemburkar et al., Organic Process Research & Development, vol. 4, 2000, pp. 413-417.
Chromatographia, 2002, vol. 55, pp. S115-S119.
Comprehensive Heterocyclic Chemistry, vol. 3, 1984, pp. 98-101 and 134.
Dunitz et al., Acc. Chem. Res., vol. 28, 1995, pp. 193-200.
EMEA 2005.

(Continued)

*Primary Examiner* — James O Wilson
*Assistant Examiner* — Alexander R Pagano
(74) *Attorney, Agent, or Firm* — Fulbright & Jaworski, L.L.P.; Scott D. Rothenberger (57) ABSTRACT

The present invention relates to novel crystalline forms of bosentan and processes for their preparation. Further, the invention relates to pharmaceutical compositions comprising said crystalline forms and use of said compositions in the treatment of patients suffering from endothelin receptor mediated disorders, for example, cardiovascular disorders such as hypertension, pulmonary hypertension, ischemia, vasospasm and angina pectoris.

28 Claims, 6 Drawing Sheets

(56) References Cited

OTHER PUBLICATIONS

Heterocyclic Compounds—The Pyrimidines, 1994, XP-002495603, pp. 397-401.
J. H. Pupart, Encyclopaedia of pharmaceutical technology, 1362-1369 (2007)ARP Apr. 20, 2013.
J. Lang, Application Note, Thermal Analysis, Perkin Elmer, 2010.
Journal of Chromatography A, 1995, vol. 712(1), pp. 75-83.
Journal of the American Society for Mass Spectrometry, 1999, vol. 10(12), pp. 1305-1314.
Journal of Mass Spectrometry, 1996, vol. 31, pp. 69-76.
Journal of Chromatography B, 2000, vol. 749(1), pp. 67-83.
Martinez-Oharriz et al., Journal of Pharmaceutical Sciences, 1994, vol. 83(2), pp. 174-177.
Modern Drug Discovery, Mar. 2000, p. 53, K. Knapman.
"Protection of a reactive group" IUPAC Gold Book 2011.
Swanepoel et al., European Journal of Pharmaceuticals and Biopharmaceutics, 2003, vol. 55, pp. 345-349.
Topics in Current Chemistry, vol. 198, 1998, pp. 163-208.
T.W. Greeene & P.G.M. Wuts, Protective Groups in Organic Synthesis ($3^{rd}$ Ed., John Wily & Sons, 1999) re hydroxyl protection.
Uses of X-ray Powder Diffraction in the Pharmaceutical Industry; in Pharmaceutical Sciences Encyclopedia: Drug Discovery, Development, and Manufacturing, Edited by Shayne C. Gad, John Wiley & Sons, 2010.
Wu et al., Journal of Pharmaceutical Sciences, 1994, vol. 83(10), pp. 1404-1406.

* cited by examiner

CRYSTALLINE FORMS OF BOSENTAN

CROSS-REFERENCE TO RELATED APPLICATION(s)

This application is a Section 371 National Stage Application of International No peaks at 2θ values 4.02, 6.12, 8.38, 9.39, 10.04, 15.26, 17.72, 17.98, 18.81, 19.28, 20.31, 21.05, 27.57, 31.91 and 45.65±0.2° θ.

Figure 1:
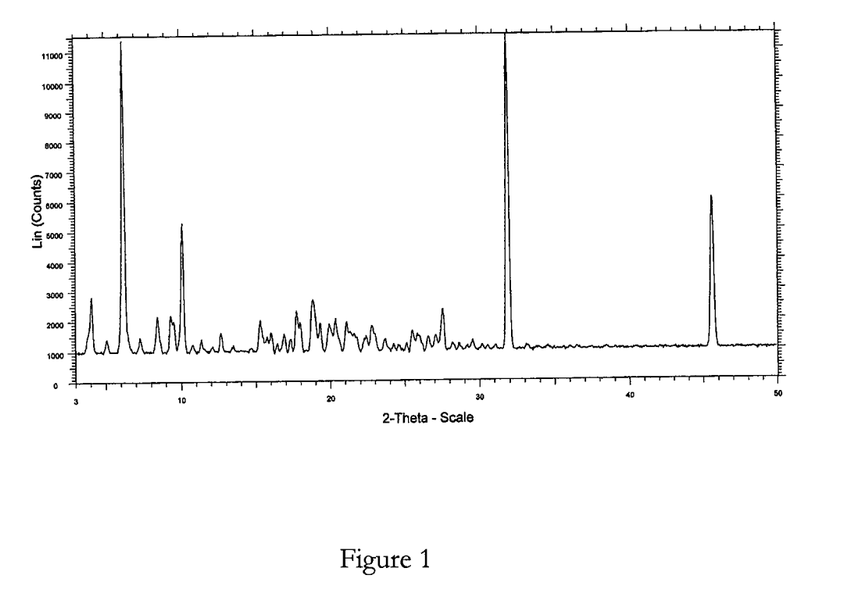
FIG. 1 represents the XRPD trace of bosentan form 5.

In a second aspect there is provided a crystalline form 5 of bosentan having an XRPD trace substantially as shown in FIG. 1.

In a third aspect of the invention a bosentan crystalline form 5 is characterized by a DSC trace comprising endothermic peaks at about 93° C. and about 196° C., preferably at about 92.65° C. and about 195.90° C., all ±2° C.

Figure 2:
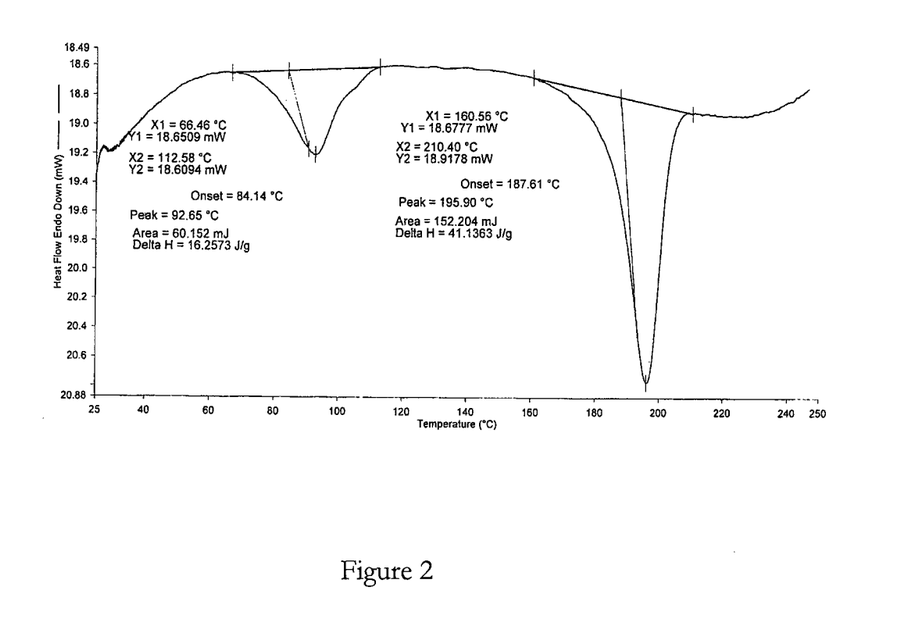
FIG. 2 represents the DSC trace of bosentan form 5.

In a fourth aspect there is provided a crystalline form 5 of bosentan having a DSC trace substantially as shown in FIG. 2.

Figure 3:
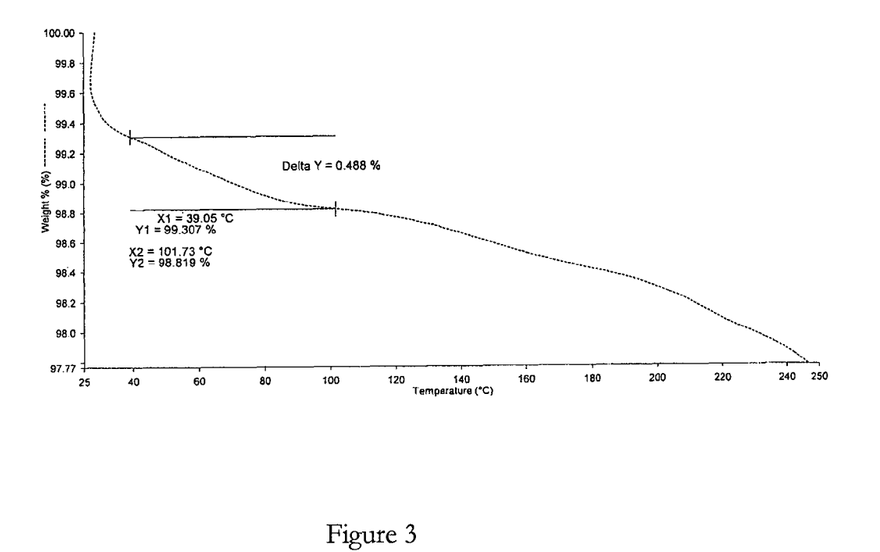
FIG. 3 represents the TGA trace of bosentan form 5.

Whilst a fifth aspect according to the invention provides a crystalline form 5 of bosentan having a TGA trace substantially as shown in FIG. 3.

Preferably the crystalline form 5 of bosentan of the present invention is substantially free of other polymorphic forms including amorphous bosentan. It preferably comprises less than 10%, preferably less than 5%, preferably less than 3%, preferably less than 2%, preferably less than 1%, preferably less than 0.5%, preferably less than 0.1% of other polymorphic forms including amorphous bosentan.

A sixth aspect according to the invention provides a process for preparing the crystalline form 5 of bosentan, comprising the steps of:
(a) dissolving bosentan in one or more organic solvent(s);
(b) causing a crystalline solid to precipitate from the solution obtained in step (a); and
(c) isolating the crystalline solid obtained from step (b).

In a preferred embodiment the solvent comprises ethyl acetoacetate. In another embodiment the solvent is heated in step (a) until a clear solution is obtained. A further embodiment provides that the crystalline solid is precipitated by cooling the solution. A further embodiment still provides that the precipitated solid is isolated by filtration and preferably the isolated solid is dried under vacuum until a constant weight is achieved.

A seventh aspect provides a process for preparing the crystalline form 5 of bosentan, comprising the steps of:
(a) heating bosentan in ethyl acetoacetate until a clear solution is obtained;
(b) cooling the solution from step (a) until a precipitate forms; and
(c) filtering the suspension from step (b) and drying the obtained solid under vacuum at about 20-40° C., preferably at about 25° C., until a constant weight is achieved.

In an eighth aspect of the invention a crystalline form 6 of bosentan is provided characterized by an X-ray diffraction pattern comprising two or more peaks (preferably three or more, four or more, five or more, or six peaks) selected from peaks at 2θ values 3.87, 7.51, 8.84, 11.14, 18.74 and 23.30±0.2° θ.

Figure 4:
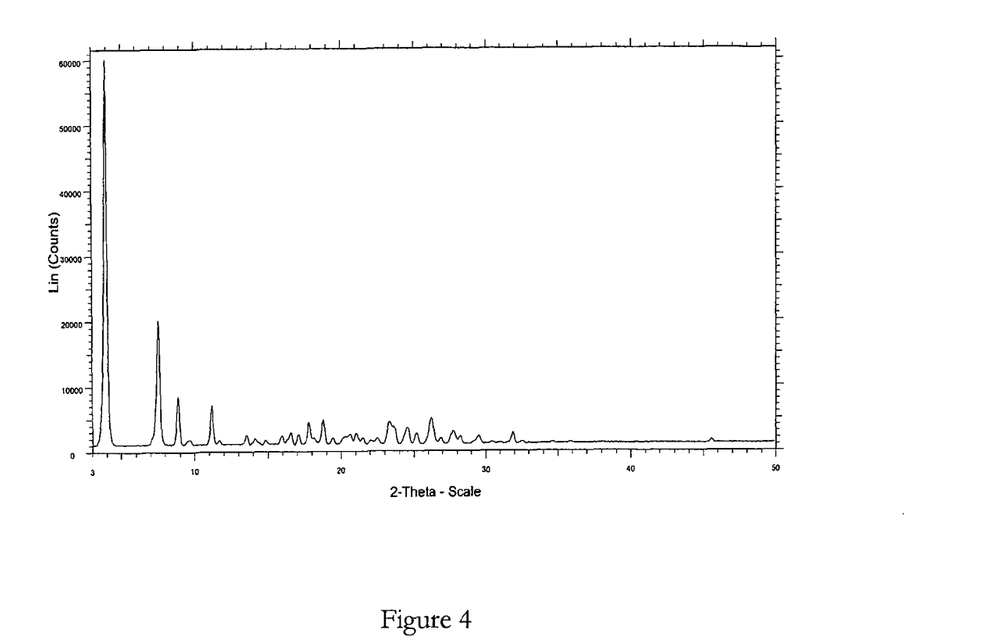
FIG. 4 represents the XRPD trace of bosentan form 6.

A ninth aspect provides a crystalline form 6 of bosentan having an XRPD trace substantially as shown in FIG. 4.

A tenth aspect provides a crystalline form 6 of bosentan characterized by a DSC trace comprising endothermic peaks at about 78° C. and about 134° C., preferably at about 77.57° C. and about 134.08° C., all ±2° C., preferably all ±0.5° C.

Figure 5:
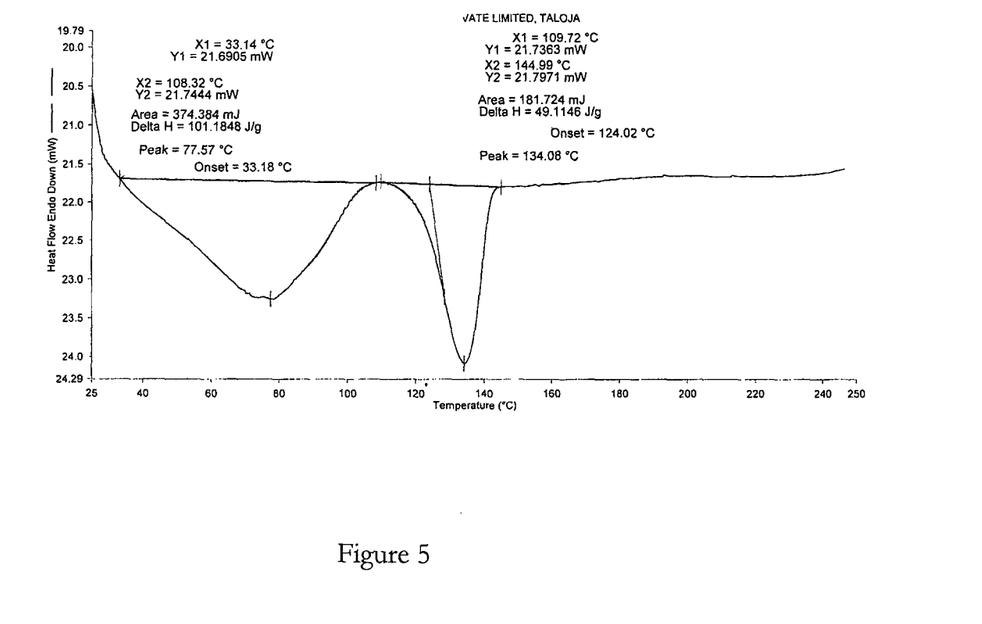
FIG. 5 represents the DSC trace of bosentan form 6.

An eleventh aspect provides a crystalline form 6 of bosentan having a DSC trace substantially as shown in FIG. 5.

Figure 6:
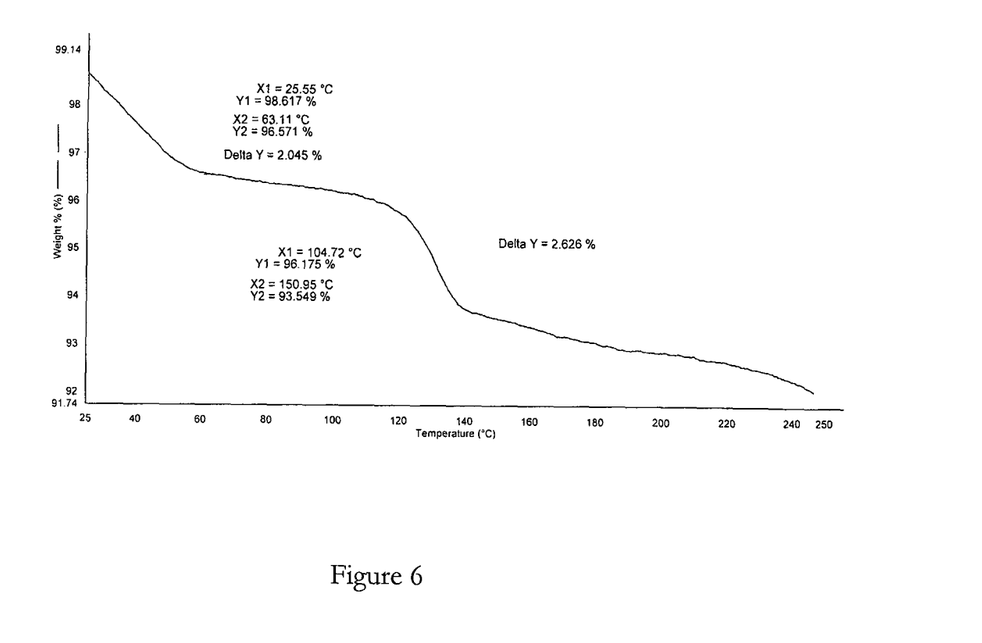
FIG. 6 represents the TGA trace of bosentan form 6.

A twelfth aspect provides a crystalline form 6 of bosentan having a TGA trace substantially as shown in FIG. 6.

Preferably the crystalline form 6 of bosentan of the present invention is substantially free of other polymorphic forms including amorphous bosentan. It preferably comprises less than 10%, preferably less than 5%, preferably less than 3%, preferably less than 2%, preferably less than 1%, preferably less than 0.5%, preferably less than 0.1% of other polymorphic forms including amorphous bosentan.

According to a thirteenth aspect of the invention there is provided a process for preparing the crystalline form 6 of bosentan, comprises the steps of:
(a) dissolving bosentan in one or more organic solvent(s) and optionally water;
(b) causing a crystalline solid to precipitate from the solution obtained in step (a); and
(c) isolating the crystalline solid obtained from step (b).

In a preferred embodiment the solvent, each solvent or one or more of the solvent(s) is a $C_1$-$C_6$ alcohol. In a particularly preferred embodiment bosentan is dissolved in step (a) by heating in butan-2-ol and amyl alcohol and adding water. In another embodiment the solid is precipitated by cooling the solution from step (a) and adding cyclohexane. Preferably, the precipitated solid is isolated by filtration, which solid is preferably dried under vacuum until a constant weight is achieved.

A fourteenth aspect according to the invention provides a process for preparing the crystalline form 6 of bosentan, comprising the steps of:
(a) dissolving or suspending bosentan in a solvent system comprising one or more $C_1$-$C_6$ alcohol(s);
(b) adding water to the solution or suspension from step (a) until a clear solution is obtained;
(c) cooling the solution from step (b) to between about 20-40° C.;
(d) adding cyclohexane to the solution from step (c) until a precipitate is formed; and
(e) filtering the resultant precipitated solid and drying under vacuum at between about 20-30° C. until a constant weight is achieved.

In a preferred embodiment the solvent system comprises butan-2-ol and amyl alcohol and preferably is heated in step (a) to about 80° C. In a fifteenth aspect of the invention a crystalline form 7 of bosentan is provided characterized by an X-ray diffraction pattern comprising two or more peaks (preferably three or more, four or more, five or more, six or more, seven or more, eight or more, nine or more, ten or more, eleven or more, twelve or more, thirteen or more, fourteen or more, fifteen or more, sixteen or more, or seventeen peaks) selected from peaks at 2θ values 3.64, 4.23, 4.95, 7.04, 7.68, 8.23, 9.05, 9.66, 10.48, 13.95, 15.20, 16.17, 17.37, 18.06, 20.03, 22.13 and 23.62±0.2° θ.

Figure 7:
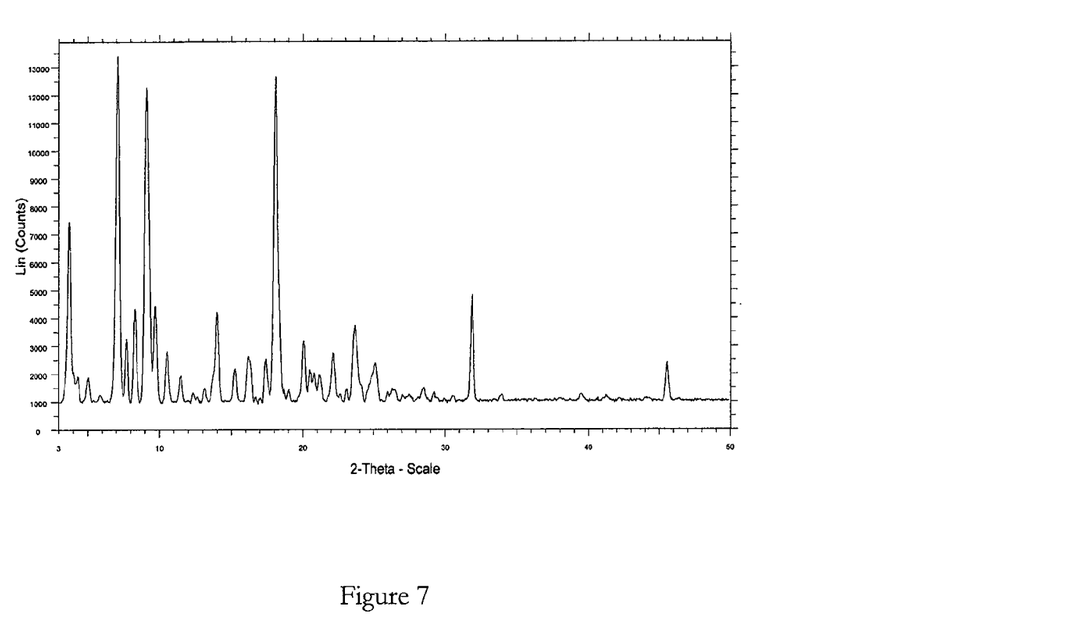
FIG. 7 represents the XRPD trace of bosentan form 7.

A sixteenth aspect provides a crystalline form 7 of bosentan having an XRPD trace substantially as shown in FIG. 7.

A seventeenth aspect provides a crystalline form 7 of bosentan characterized by a DSC trace comprising endothermic peaks at about 75° C. and about 130° C., preferably at about 74.58° C. and about 129.99° C., all ±2° C.

Figure 8:
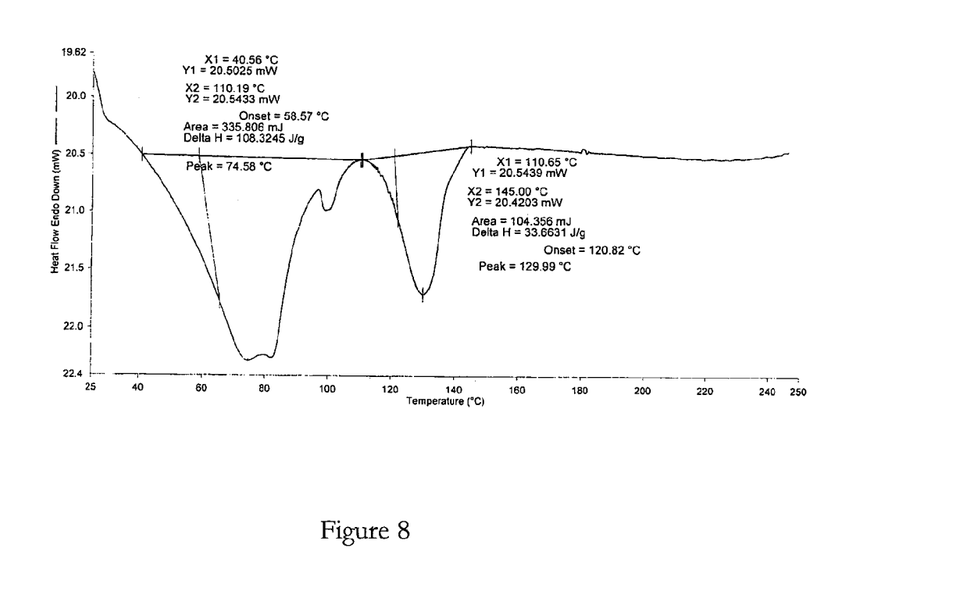
FIG. 8 represents the DSC trace of bosentan form 7.

An eighteenth aspect provides a crystalline form 7 of bosentan having a DSC trace substantially as shown in FIG. 8.

Figure 9:
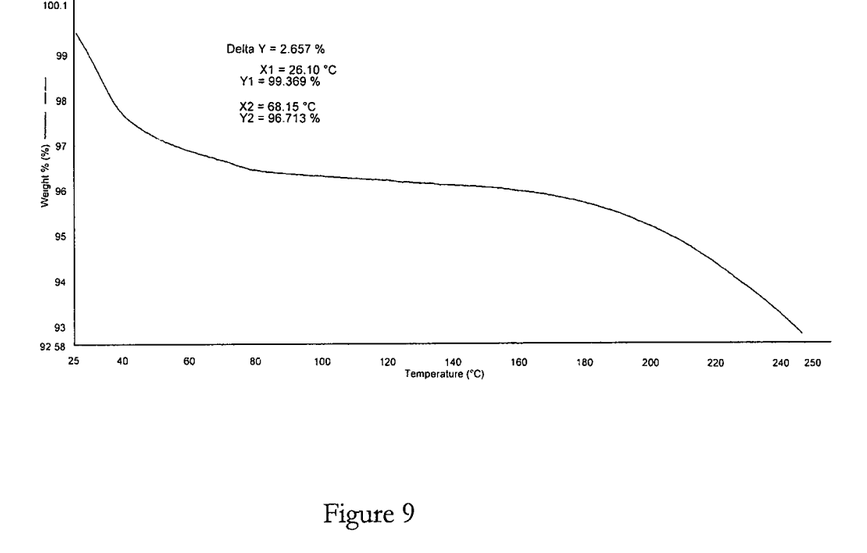
FIG. 9 represents the TGA trace of bosentan form 7.

A nineteenth aspect of the invention provides a crystalline form 7 of bosentan having a TGA trace substantially as shown in FIG. 9.

Preferably the crystalline form 7 of bosentan of the present invention is substantially free of other polymorphic forms including amorphous bosentan. It preferably comprises less than 10%, preferably less than 5%, preferably less than 3%, preferably less than 2%, preferably less than 1%, preferably less than 0.5%, preferably less than 0.1% of other polymorphic forms including amorphous bosentan.

A twentieth aspect provides a process for preparing the crystalline form 7 of bosentan, comprising the steps of:
(a) dissolving bosentan in one or more organic solvent(s);
(b) causing a crystalline solid to precipitate from the solution obtained in step (a); and
(c) isolating the crystalline solid obtained from step (b).

In a preferred embodiment, bosentan is dissolved in the or each solvent until a clear solution is obtained. Preferably, bosentan is dissolved in step (a) by heating the or each solvent. In another preferred embodiment the, each or one or more of the solvent(s) is a $C_1$-$C_6$ alcohol. Most preferably, the solvents are a mixture of cyclohexanone and n-butanol or, alternatively, the solvents are a mixture of cyclohexanone and ethanol. In a further embodiment, the crystalline solid is precipitated by adding n-hexane to the solution from step (a). Preferably, the solid is isolated by filtration, more preferably the isolated solid is dried under vacuum until a constant weight is achieved.

In a twenty-first aspect of the invention there is provided a process for preparing the crystalline form 7 of bosentan, comprising the steps of:
(a) dissolving bosentan in a mixture of cyclohexanone and a $C_1$-$C_6$ alcohol;
(b) cooling the solution from step (a) to about 30° C. within about 30 minutes whilst stirring;
(c) adding n-hexane to the solution from step (b) to form a precipitate and stirring the suspension for about 2-5 hours; and
(d) filtering the suspension from step (c) and drying the obtained solid under vacuum at about 20-40° C., preferably at about 25° C., until a constant weight is achieved.

In a preferred embodiment the $C_1$-$C_6$ alcohol is n-butanol. Preferably bosentan is dissolved in step (a) by heating the mixture until a clear solution is obtained, preferably at about 50° C.

Alternatively, in a twenty-second aspect of the invention there is provided a process for preparing the crystalline form 7 of bosentan, comprising the steps of:
(a) dissolving bosentan in a mixture of cyclohexanone and a $C_1$-$C_6$ alcohol;
(b) cooling the solution from step (a) to about 30° C. within about 20 minutes whilst stirring;
(c) adding n-hexane to the solution from step (b) to form a precipitate and stirring the suspension for between about 15-25 hours; and
(d) filtering the suspension from step (c) and drying the obtained solid under vacuum at about 20-40° C., preferably at about 25° C., until a constant weight is achieved.

In a particularly preferred embodiment the $C_1$-$C_6$ alcohol is ethanol. Preferably bosentan is dissolved in step (a) by heating the mixture until a clear solution is obtained, preferably at about 80° C.

A twenty-third aspect according to the invention provides a crystalline form 8 of bosentan characterized by an X-ray diffraction pattern comprising two or more peaks (preferably three or more, four or more, five or more, six or more, seven or more, eight or more, nine or more, ten or more, eleven or more, twelve or more, thirteen or more, fourteen or more, fifteen or more, sixteen or more, seventeen or more, or eighteen peaks) selected from peaks at 2θ values 9.47, 13.41, 14.52, 15.46, 15.73, 16.35, 16.88, 17.99, 18.87, 19.25, 20.53, 21.82, 23.02, 23.83, 24.61, 24.86, 25.13 and 26.03±0.2° θ

In an alternative embodiment, the twenty-third aspect according to the invention provides a crystalline form 8 of bosentan characterized by an X-ray diffraction pattern comprising two or more peaks (preferably three or more, or four peaks) selected from peaks at 2θ values 3.73, 7.43, 14.95 and 19.78±0.2° θ.

Figure 10:
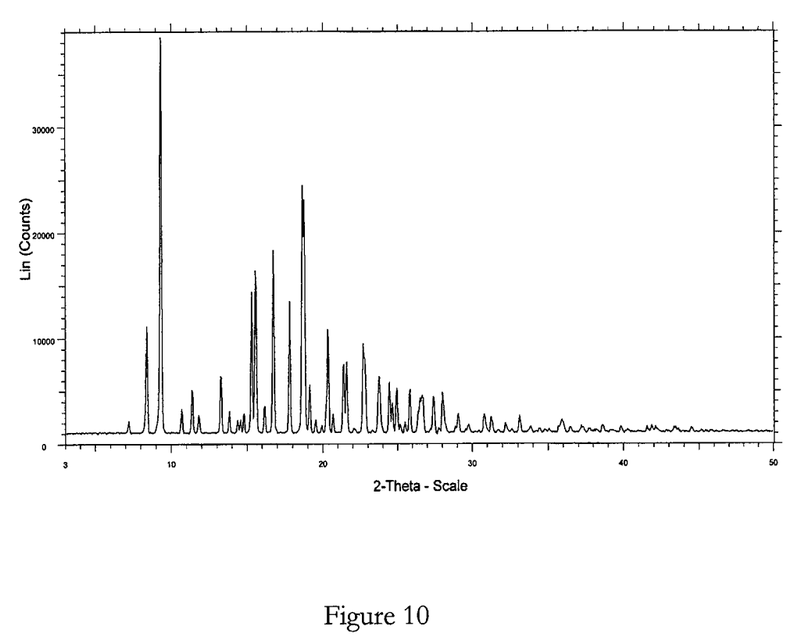
FIG. 10 represents the XRPD trace of bosentan form 8.

A twenty-fourth aspect provides a crystalline form 8 of bosentan having an XRPD trace substantially as shown in FIG. 10.

A twenty-fifth aspect provides a crystalline form 8 of bosentan characterized by a DSC trace comprising endothermic peaks at about 58° C. and about 110° C., preferably at about 58.29° C. and about 109.55° C., all ±2° C.

Figure 11:
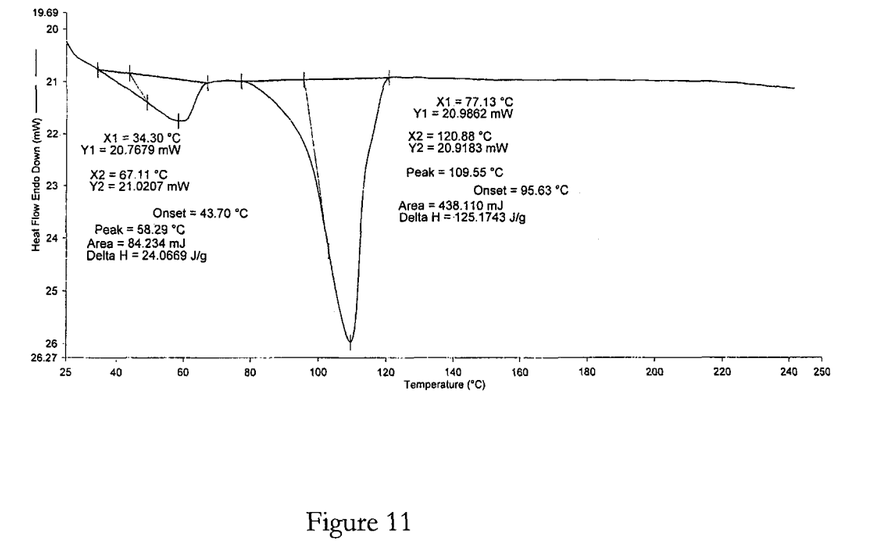
FIG. 11 represents the DSC trace of bosentan form 8.

A twenty-sixth aspect provides a crystalline form 8 of bosentan having a DSC trace substantially as shown in FIG. 11.

Figure 12:
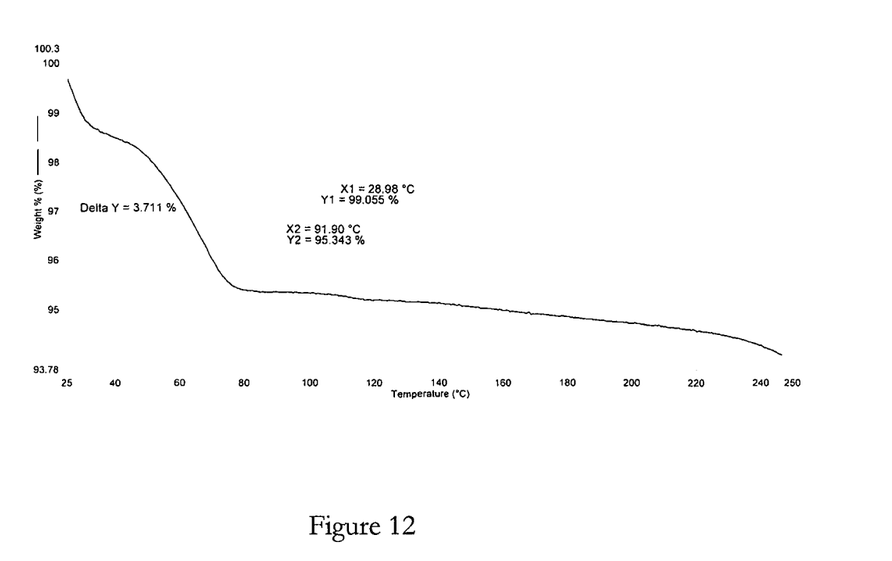
FIG. 12 represents the TGA trace of bosentan form 8.

A twenty-seventh aspect provides a crystalline form 8 of bosentan having a TGA trace substantially as shown in FIG. 12.

Preferably the crystalline form 8 of bosentan of the present invention is substantially free of other polymorphic forms including amorphous bosentan. It preferably comprises less than 10%, preferably less than 5%, preferably less than 3%, preferably less than 2%, preferably less than 1%, preferably less than 0.5%, preferably less than 0.1% of other polymorphic forms including amorphous bosentan.

A twenty-eighth aspect provides a process for preparing the crystalline form 8 of bosentan, comprising the steps of:
(a) mixing bosentan in one or more organic solvent(s);
(b) filtering the mixture from step (a); and
(c) isolating the crystalline solid from the filtrate obtained in step (b).

Preferably the process of the twenty-eighth aspect comprises the steps of:
(a) mixing bosentan in one or more organic solvent(s);
(b) filtering the mixture from step (a);
(c) causing a crystalline solid to precipitate from the filtrate obtained in step (b); and
(d) isolating the crystalline solid obtained in step (c).

Preferably, bosentan is heated in step (a) in a mixture of ethyl acetoacetate, octanol and n-pentyl acetate. In another embodiment in step (b) the mixture is filtered hot under vacuum. In another preferred embodiment the crystalline solid is obtained by cooling the filtrate in step (c). Further preferred embodiments provide that the crystalline solid is further filtered and dried under vacuum until a constant weight is achieved.

A twenty-ninth aspect provides a process for preparing the crystalline form 8 of bosentan, comprising the steps of:
(a) heating bosentan in a mixture of ethyl acetoacetate, octanol and n-pentyl acetate to about 90-110° C., preferably about 100° C.;
(b) filtering the solution from step (a) under vacuum;
(c) cooling the filtrate from step (b) until a precipitate forms; and
(d) filtering the precipitate from step (c) and drying said precipitate under vacuum at about 20-40° C., preferably at about 25° C., until a constant weight is achieved.

Preferably the bosentan crystalline form 5, form 6, form 7 and form 8 of the present invention is suitable for use in medicine, preferably for treating or preventing an endothelin receptor mediated disorder. In one embodiment the endothelin receptor mediated disorder is a cardiovascular disorder. Preferably, the cardiovascular disorder is hypertension, pulmonary hypertension, ischemia, vasospasm or angina pectoris, most preferably pulmonary arterial hypertension.

A thirtieth aspect of the present invention provides a pharmaceutical composition comprising any one or a combination of bosentan crystalline form 5, form 6, form 7 or form 8, and further comprising one or more pharmaceutically acceptable excipients. Preferably the pharmaceutical composition is suitable for treating or preventing an endothelin receptor mediated disorder. In one embodiment the endothelin receptor mediated disorder is a cardiovascular disorder. Preferably, the cardiovascular disorder is hypertension, pulmonary hypertension, ischemia, vasospasm or angina pectoris, most preferably pulmonary arterial hypertension.

A thirty-first aspect of the present invention provides the use of any one or a combination of bosentan crystalline form 5, form 6, form 7 or form 8, or the use of a composition according to the thirtieth aspect of the present invention for the treatment or prevention of an endothelin receptor mediated disorder. In one embodiment the endothelin receptor mediated disorder is a cardiovascular disorder. Preferably, the cardiovascular disorder is hypertension, pulmonary hypertension, ischemia, vasospasm or angina pectoris, most preferably pulmonary arterial hypertension.

A thirty-second aspect of the present invention provides a method of treating or preventing an endothelin receptor mediated disorder, comprising administering to a patient in need thereof a therapeutically or prophylactically effective amount of any one or a combination of bosentan crystalline form 5, form 6, form 7 or form 8, or of a composition according to the thirtieth aspect of the present invention. In one embodiment the endothelin receptor mediated disorder is a cardiovascular disorder. Preferably, the cardiovascular disorder is hypertension, pulmonary hypertension, ischemia, vasospasm or angina pectoris, most preferably pulmonary arterial hypertension. Preferably the patient is a mammal, preferably a human.

DETAILED DESCRIPTION OF THE INVENTION

The present invention provides novel crystalline forms 5-8 of bosentan. The processes disclosed herein for preparing said forms are capable of providing these crystalline forms of the invention with consistent polymorphic purity irrespective of the scale of preparation. Embodiments of the invention related to the preparation of the forms 5-8 generally involve the dissolution of an amount of bosentan starting material in one or a mixture of organic solvents. It is envisaged that any form of bosentan known or unknown even any amorphous forms may be used as the initial bosentan starting material.

In preferred embodiments of the processes for preparing forms 5-8 of bosentan according to the invention, the starting material is dissolved or suspended in a solvent, preferably an organic solvent. In embodiments where the bosentan starting material is dissolved, any technique known to the skilled person may be employed to dissolve the bosentan. In preferred embodiments, heating the bosentan starting material in the desired solvent or solvents until a clear solution is obtained is preferred. In further embodiments, the desired crystalline form is crystallised by cooling the crystallisation solution and/or adding an appropriate anti-solvent. The skilled person will understand, of course, that the cooling of the solution is performed to allow the desired crystalline form to precipitate from the solution, thus any temperature that allows such precipitation is within the scope of this invention. Preferably the crystallisation solution is then stirred. A crystallisation solution may be stirred for any of a number of reasons known to the skilled person, for example, to allow uniform dispersion of heat during cooling, or to provide a homogenous slurry. The stirring may be effected by any means known in the art, for example, by a magnetic stirrer or paddle stirrer. The final stages of preparing crystalline forms 5-8 according to the invention generally involve the isolation of the desired crystalline form. In preferred embodiments this may include filtering the desired crystalline form from the crystallisation suspension. In certain embodiments, the desired isolated crystalline form according to the invention is then dried. Preferably, the desired crystalline form according to the invention is dried until a constant weight is achieved. In particularly preferred embodiments the desired crystalline form is dried under vacuum at about room temperature or between 20 and 35° C.

A further embodiment of the invention provides compositions of crystalline forms 5-8 according to the invention and further comprising one or more pharmaceutically acceptable excipient(s). Another aspect of the present invention is the use of pharmaceutical compositions comprising one or more of the novel forms 5-8 according to the invention to treat patients suffering from endothelin receptor mediated disorders, in particular cardiovascular disorders such as hypertension, ischemia, vasospasm, angina pectoris and pulmonary hypertension.

A further embodiment of the invention is a process for making a pharmaceutical composition comprising mixing a crystalline form of bosentan according to the invention and one or more pharmaceutically acceptable excipients. In one embodiment of the invention, there is provided a method for the treatment of an endothelin receptor mediated disorder comprising administering to a subject in need thereof a composition comprising a therapeutically effective amount of a crystalline form of bosentan according to the invention. In a further embodiment according to the invention, there is provided the use of a crystalline form of bosentan according to the invention substantially free of other polymorphic forms, for the preparation of a medicament for treating an endothelin receptor mediated disorder. Preferably the disorder is pulmonary hypertension. In preferred embodiments the purity is in the order of bosentan form 5, form 6, form 7 or form 8 comprising less than 10%, preferably less than 5%, more preferably less 1%, most preferably less than 0.1% of any other known or unknown crystalline or amorphous forms of bosentan.

Illustrative of the invention is a pharmaceutical composition comprising a novel crystalline form of bosentan according to the invention and one or more pharmaceutically acceptable excipient(s). Said composition may comprise solid pharmaceutical compositions which in certain embodiments may comprise tablets including, for example, oral dispersible tablets, capsules containing pellets, mini-tablets, powders or mixtures thereof, caplets, or any of the solid dosage forms that are within the repertoire of the skilled formulation scientist. These may further include immediate release forms of the above solid dosage forms or controlled release forms of the above including sustained release, delayed release and prolonged release compositions. It is also envisaged that the invention comprises liquid formulations which may be prepared by mixing the crystalline forms according to the invention with a pharmaceutically suitable liquid carrier of solvent.

In one embodiment of the invention there is provided a method for the treatment of an endothelin receptor mediated disorder in a subject in need thereof, comprising administering to the subject a composition comprising a therapeutically effective amount of a novel polymorph of bosentan according to the invention. In a further embodiment according to the invention there is provided the use of a novel polymorph of bosentan according to the invention substantially free of other crystalline and amorphous forms, for the preparation of a medicament for treating an endothelin receptor mediated disorder in a subject in need thereof, preferably the purity is in the order of bosentan form 5, form 6, form 7 or form 8 comprising less than 10%, preferably less than 5%, more preferably less than 1%, most preferably less than 0.1% of other forms of bosentan.

In addition to the active ingredient(s), the pharmaceutical compositions of the present invention may, as alluded to above, contain one or more excipients. Excipients are added to the composition for a variety of purposes. Diluents increase the bulk of a solid pharmaceutical composition and may make a pharmaceutical dosage form containing the composition easier for the patient and care giver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. Carbopol®), carboxymethyl cellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminium silicate, maltodextrin, methyl cellulose, polymethacrylates, povidone (e.g. Kollidon®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethyl cellulose calcium, carboxymethyl cellulose sodium (e.g. Ac-Di-Sol®, Primellose®), colloidal silicon dioxide, croscarmellose sodium, crospovidone (e.g. Kollidon®, Polyplasdone®), guar gum, magnesium aluminium silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and die. Some excipients and active ingredients have a tendency to adhere to the surfaces of the punch and die, which can cause the product to have pitting and other surface irregularities. A lubricant can be added to the composition to reduce adhesion and ease the release of the product from the die. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavouring agents and flavour enhancers make the dosage form more palatable to the patient. Common flavouring agents and flavour enhancers for pharmaceutical products that may be included in the composition of the present invention include maltol, vanillin, ethyl vanillin, menthol, citric acid, fumaric acid, ethyl maltol and tartaric acid.

Solid and liquid compositions may also be dyed using any pharmaceutically acceptable colorant to improve their appearance and/or facilitate patient identification of the product and unit dosage level.

In liquid pharmaceutical compositions of the present invention, the crystalline bosentan and any other solid excipients are dissolved or suspended in a liquid carrier such as water, vegetable oil, alcohol, polyethylene glycol, propylene glycol or glycerine.

Liquid pharmaceutical compositions may further contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention may also contain a viscosity enhancing agent to improve the mouth-feel or organoleptic qualities of the product and/or coat the lining of the gastrointestinal tract. Such agents include acacia, alginic acid, bentonite, carbomer, carboxymethyl cellulose calcium or sodium, cetostearyl alcohol, methyl cellulose, ethyl cellulose, gelatin, guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Preservatives and chelating agents such as alcohol, sodium benzoate, butylated hydroxytoluene, butylated hydroxyanisole and ethylenediaminetetraacetic acid may be added at levels safe for ingestion to improve storage stability.

According to the present invention, a liquid composition may also contain a buffer such as gluconic acid, lactic acid, citric acid or acetic acid, sodium gluconate, sodium lactate, sodium citrate or sodium acetate.

Selection of excipients and the amounts used may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts. Dosage forms include solid dosage forms like tablets, powders, capsules, suppositories, sachets, troches and lozenges, as well as liquid syrups, suspensions and elixirs.

The dosage form of the present invention may be a capsule containing the composition, preferably a powdered or granulated solid composition of the invention, within either a hard or a soft shell. The shell may be made from gelatin and optionally contain a plasticizer such as glycerine and sorbitol, and an opacifying agent or colourant. The active ingredient and excipients may be formulated into compositions and dosage forms according to methods known in the art.

A composition for tableting or capsule filling may be prepared by wet granulation. In wet granulation, some or all of the active ingredient and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

In further embodiments, the composition of the invention may further comprise one or more additional active ingredients.

The following paragraphs enumerated consecutively from 1 through 78 provide for various aspects of the present invention. In one embodiment, the present invention provides:

1. Crystalline form 5 of bosentan characterized by an X-ray diffraction pattern comprising two or more peaks selected from peaks at 2θ values 4.02, 6.12, 8.38, 9.39, 10.04, 15.26, 17.72, 17.98, 18.81, 19.28, 20.31, 21.05, 27.57, 31.91 and 45.65±0.2° θ.
2. Crystalline form 5 of bosentan having an XRPD trace substantially as shown in FIG. 1.
3. Crystalline form 5 of bosentan characterized by a DSC trace comprising endothermic peaks at about 93° C.±2° C. and about 196° C.±2° C.
4. Crystalline form 5 of bosentan having a DSC trace substantially as shown in FIG. 2.
5. Crystalline form 5 of bosentan having a TGA trace substantially as shown in FIG. 3.
6. A process for preparing crystalline form 5 of bosentan according to any one of paragraphs 1-5, comprising the steps of:
(a) dissolving bosentan in one or more organic solvent(s);
(b) causing a crystalline solid to precipitate from the solution obtained in step (a); and
(c) isolating the crystalline solid obtained from step (b).
7. A process according to paragraph 6, wherein the solvent in step (a) comprises ethyl acetoacetate.
8. A process according to paragraph 6 or 7, wherein the solvent is heated in step (a) until a clear solution is obtained.
9. A process according to any one of paragraphs 6-8, wherein the crystalline solid is precipitated in step (b) by cooling the solution.
10. A process according to any one of paragraphs 6-9, wherein the precipitated solid is isolated in step (c) by filtration.
11. A process according to any one of paragraphs 6-10, wherein the isolated solid from step (c) is dried under vacuum until a constant weight is achieved.
12. A process for preparing crystalline form 5 of bosentan according to any one of paragraphs 1-5, comprising the steps of:
(a) heating bosentan in ethyl acetoacetate until a clear solution is obtained;
(b) cooling the solution from step (a) until a precipitate forms; and
(c) filtering the suspension from step (b) and drying the obtained solid under vacuum at about 20-40° C. until a constant weight is achieved.
13. Crystalline form 6 of bosentan characterized by an X-ray diffraction pattern comprising two or more peaks selected from peaks at 2θ values 3.87, 7.51, 8.84, 11.14, 18.74 and 23.30±0.2° θ.
14. Crystalline form 6 of bosentan having an XRPD trace substantially as shown in FIG. 4.
15. Crystalline form 6 of bosentan characterized by a DSC trace comprising endothermic peaks at about 78° C.±2° C. and about 134° C.±2° C.
16. Crystalline form 6 of bosentan having a DSC trace substantially as shown in FIG. 5.
17. Crystalline form 6 of bosentan having a TGA trace substantially as shown in FIG. 6.
18. A process for preparing crystalline form 6 of bosentan according to any one of paragraphs 13-17, comprising the steps of:
(a) dissolving bosentan in one or more organic solvent(s) and optionally water;
(b) causing a crystalline solid to precipitate from the solution obtained in step (a); and
(c) isolating the crystalline solid obtained from step (b).
19. A process according to paragraph 18, wherein the solvent, each solvent or one or more of the solvent(s) in step (a) is a $C_1$-$C_6$ alcohol.
20. A process according to paragraph 18 or 19, wherein bosentan is dissolved in step (a) by heating in butan-2-ol and amyl alcohol and adding water.
21. A process according to any one of paragraphs 18-20, wherein the solid is precipitated in step (b) by cooling the solution from step (a) and adding cyclohexane.
22. A process according to any one of paragraphs 18-21, wherein the precipitated solid from step (b) is isolated by filtration.
23. A process according to any one of paragraphs 18-22, wherein the isolated solid from step (c) is dried under vacuum until a constant weight is achieved.
24. A process for preparing crystalline form 6 of bosentan according to any one of paragraphs 13-17, comprising the steps of:

(a) dissolving or suspending bosentan in a solvent system comprising one or more $C_1$-$C_6$ alcohol(s);
(b) adding water to the solution or suspension from step (a) until a clear solution is obtained;
(c) cooling the solution from step (b) to between about 20-40° C.;
(d) adding cyclohexane to the solution from step (c) until a precipitate is formed; and
(e) filtering the resultant precipitated solid and drying under vacuum at between about 20-30° C. until a constant weight is achieved.

25. A process according to paragraph 24, wherein the solvent system in step (a) comprises butan-2-ol and amyl alcohol.

26. A process according to paragraph 24 or 25, wherein the solvents are heated in step (a) to about 80° C.

27. Crystalline form 7 of bosentan characterized by an X-ray diffraction pattern comprising two or more peaks selected from peaks at 2θ values 3.64, 4.23, 4.95, 7.04, 7.68, 8.23, 9.05, 9.66, 10.48, 13.95, 15.20, 16.17, 17.37, 18.06, 20.03, 22.13 and 23.62±0.2° θ.

28. Crystalline form 7 of bosentan having an XRPD trace substantially as shown in FIG. 7.

29. Crystalline form 7 of bosentan characterized by a DSC trace comprising endothermic peaks at about 75° C.±2° C. and about 130° C.±2° C.

30. Crystalline form 7 of bosentan having a DSC trace substantially as shown in FIG. 8.

31. Crystalline form 7 of bosentan having a TGA trace substantially as shown in FIG. 9.

32. A process for preparing crystalline form 7 of bosentan according to any one of paragraphs 27-31, comprising the steps of:
(a) dissolving bosentan in one or more organic solvent(s);
(b) causing a crystalline solid to precipitate from the solution obtained in step (a); and
(c) isolating the crystalline solid obtained from step (b).

33. A process according to paragraph 32, wherein bosentan is dissolved in step (a) in the or each solvent until a clear solution is obtained.

34. A process according to paragraph 32 or 33, wherein bosentan is dissolved in step (a) by heating the or each solvent.

35. A process according to any one of paragraphs 32-34, wherein the solvent, each solvent or one or more of the solvent(s) in step (a) is a $C_1$-$C_6$ alcohol.

36. A process according to any one of paragraphs 32-35, wherein the solvents in step (a) are a mixture of cyclohexanone and n-butanol.

37. A process according to any one of paragraphs 32-35, wherein the solvents in step (a) are a mixture of cyclohexanone and ethanol.

38. A process according to any one of paragraphs 32-37, wherein the crystalline solid is precipitated by adding n-hexane to the solution from step (a).

39. A process according to any one of paragraphs 32-38, wherein the solid is isolated in step (c) by filtration.

40. A process according to any one of paragraphs 32-39, wherein the isolated solid from step (c) is dried under vacuum until a constant weight is achieved.

41. A process for preparing crystalline form 7 of bosentan according to any one of paragraphs 27-31, comprising the steps of:
(a) dissolving bosentan in a mixture of cyclohexanone and a $C_1$-$C_6$ alcohol;
(b) cooling the solution from step (a) to about 30° C. within about 30 minutes whilst stirring;
(c) adding n-hexane to the solution from step (b) to form a precipitate and stirring the suspension for about 2-5 hours; and
(d) filtering the suspension from step (c) and drying the obtained solid under vacuum at about 20-40° C. until a constant weight is achieved.

42. A process according to paragraph 41, wherein the $C_1$-$C_6$ alcohol in step (a) is n-butanol.

43. A process according to paragraph 41 or 42, wherein bosentan is dissolved in step (a) by heating the mixture until a clear solution is obtained.

44. A process for preparing crystalline form 7 of bosentan according to any one of paragraphs 27-31, comprising the steps of:
(a) dissolving bosentan in a mixture of cyclohexanone and a $C_1$-$C_6$ alcohol;
(b) cooling the solution from step (a) to about 30° C. within about 30 minutes whilst stirring;
(c) adding n-hexane to the solution from step (b) to form a precipitate and stirring the suspension for between about 15-25 hours; and
(d) filtering the suspension from step (c) and drying the obtained solid under vacuum at about 20-40° C. until a constant weight is achieved.

45. A process according to paragraph 44, wherein the $C_1$-$C_6$ alcohol in step (a) is ethanol.

46. A process according to paragraph 44 or 45, wherein bosentan is dissolved in step (a) by heating the mixture until a clear solution is obtained.

47. Crystalline form 8 of bosentan characterized by an X-ray diffraction pattern comprising two or more peaks selected from peaks at 2θ values 9.47, 13.41, 14.52, 15.46, 15.73, 16.35, 16.88, 17.99, 18.87, 19.25, 20.53, 21.82, 23.02, 23.83, 24.61, 24.86, 25.13 and 26.03±0.2° θ.

48. Crystalline form 8 of bosentan having an XRPD trace substantially as shown in FIG. 10.

49. Crystalline form 8 of bosentan characterized by a DSC trace comprising endothermic peaks at about 58° C.±2° C. and about 110° C.±2° C.

50. Crystalline form 8 of bosentan having a DSC trace substantially as shown in FIG. 11.

51. Crystalline form 8 of bosentan having a TGA trace substantially as shown in FIG. 12.

52. A process for preparing crystalline form 8 of bosentan according to any one of paragraphs 47-51, comprising the steps of:
(a) mixing bosentan in one or more organic solvent(s);
(b) filtering the mixture from step (a);
(c) causing a crystalline solid to precipitate from the filtrate obtained in step (b); and
(d) isolating the crystalline solid obtained in step (c).

53. A process according to paragraph 52, wherein bosentan is heated in step (a) in a mixture of ethyl acetoacetate, octanol and n-pentyl acetate.

54. A process according to paragraph 52 or 53, wherein in step (b) the mixture is filtered under vacuum whilst still hot.

55. A process according to any one of paragraphs 52-54, wherein the crystalline solid is obtained by cooling the filtrate in step (c).

56. A process according to any one of paragraphs 52-55, wherein the crystalline solid is filtered in step (d) and dried under vacuum until a constant weight is achieved.

57. A process for preparing crystalline form 8 of bosentan according to any one of paragraphs 47-51, comprising the steps of:
(a) dissolving bosentan in a mixture of ethyl acetoacetate, octanol and n-pentyl acetate;

(b) filtering the solution from step (a) under vacuum;
(c) cooling the filtrate from step (b) until a precipitate forms; and
(d) filtering the precipitate from step (c) and drying said precipitate under vacuum at about 20-40° C. until a constant weight is achieved.

58. A process according to paragraph 57, wherein bosentan is dissolved in step (a) by heating the mixture to about 90-110° C.

59. A crystalline form of bosentan according to any one of paragraphs 1-5, 13-17, 27-31 or 47-51, comprising less than 10% of other forms of bosentan.

60. A crystalline form of bosentan according to paragraph 59, comprising less than 5% of other forms of bosentan.

61. A crystalline form of bosentan according to paragraph 60, comprising less than 1% of other forms of bosentan.

62. A crystalline form of bosentan according to paragraph 61, comprising less than 0.1% of other forms of bosentan.

63. A crystalline form of bosentan according to any one of paragraphs 1-5, 13-17, 27-31, 47-51 or 59-62, for use in medicine.

64. A crystalline form of bosentan according to paragraph 63, for treating or preventing an endothelin receptor mediated disorder.

65. A crystalline form of bosentan according to paragraph 64, wherein the endothelin receptor mediated disorder is a cardiovascular disorder.

66. A crystalline form of bosentan according to paragraph 65, wherein the cardiovascular disorder is hypertension, pulmonary hypertension, ischemia, vasospasm or angina pectoris.

67. A crystalline form of bosentan according to paragraph 66, wherein the cardiovascular disorder is pulmonary arterial hypertension.

68. A pharmaceutical composition comprising one or more crystalline forms of bosentan according to any one of paragraphs 1-5, 13-17, 27-31, 47-51 or 59-67, and one or more pharmaceutically acceptable excipients.

69. Use of one or more crystalline forms of bosentan according to any one of paragraphs 1-5, 13-17, 27-31, 47-51 or 59-67, or use of a composition according to paragraph 68, for the treatment or prevention of an endothelin receptor mediated disorder.

70. Use according to paragraph 69, for the treatment or prevention of a cardiovascular disorder.

71. Use according to paragraph 70, wherein the cardiovascular disorder is hypertension, pulmonary hypertension, ischemia, vasospasm or angina pectoris.

72. Use according to paragraph 71, wherein the cardiovascular disorder is pulmonary arterial hypertension.

73. A method of treating or preventing an endothelin receptor mediated disorder, comprising administering to a patient in need thereof a therapeutically or prophylactically effective amount of one or more crystalline forms of bosentan according to any one of paragraphs 1-5, 13-17, 27-31, 47-51 or 59-67, or of a composition according to paragraph 68.

74. A method according to paragraph 73, wherein the endothelin receptor mediated disorder is a cardiovascular disorder.

75. A method according to paragraph 74, wherein the cardiovascular disorder is hypertension, pulmonary hypertension, ischemia, vasospasm or angina pectoris.

76. A method according to paragraph 75, wherein the cardiovascular disorder is pulmonary arterial hypertension.

77. A method according to any one of paragraphs 73-76, wherein the patient is a mammal.

78. A method according to paragraph 77, wherein the mammal is a human.

The details of the invention, its objects and advantages are explained hereunder in greater detail in relation to non-limiting exemplary illustrations.

EXAMPLES

The following examples describe specific methods for preparing crystalline forms of bosentan according to the invention. In all the examples below the starting material comprises 1 g of bosentan form 1 as prepared using the procedure described in WO 01/55120.

Example 1

Method for Preparing Bosentan Form 5

A mixture of bosentan and ethyl acetoacetate (5 volumes, (vol)) was heated to 50° C. until a clear solution was obtained. The solution was then cooled to about 30° C. within about 50 minutes and stirred at that temperature for about 17 hours. The resulting suspension was then filtered to obtain the desired crystalline solid and said solid was dried under vacuum at 25° C. for about 4 hours or until a constant weight was achieved.
XRPD and DSC analysis data confirmed that the product obtained was bosentan form 5.
Molar yield=0.18 g
Chemical purity>99% (measured by HPLC)
Polymorphic purity=high (measured by DSC)

Example 2

Method for Preparing Bosentan Form 6

A mixture of bosentan, butan-2-ol (2.6 vol) and amyl alcohol (2.6 vol) was heated to about 80° C., resulting in a suspension of the bosentan in the solvents. Water (1 vol) was added to this suspension to effect dissolution of the bosentan and a clear solution was obtained. The solution was then cooled to 30° C. within about 45 minutes. Cyclohexane (10 vol) was added to this cooled solution and stirred whilst the temperature was maintained at about 30° C. for about 30 minutes. The resulting suspension was then filtered to obtain the desired crystalline solid and said solid was dried under vacuum at 25° C. for about 2 hours or until a constant weight was achieved.
XRPD and DSC analysis data confirmed that the product obtained was bosentan form 6.
Molar yield=0.81 g
Chemical purity>99% (measured by HPLC)
Polymorphic purity=high (measured by DSC)

Example 3

Method for Preparing Bosentan Form 7

A mixture of bosentan, cyclohexanone (2 vol) and n-butanol (2 vol) was heated to about 50° C. to obtain a clear solution. This solution was cooled to about 30° C. within about 30 minutes and stirred at this temperature for 30 minutes. n-Hexane (15 vol) was then added to the cooled solution resulting in a solid precipitate. The suspension was further stirred for about 2.5 hours. The suspension was then filtered to obtain the desired crystalline solid and said solid was dried under vacuum at 25° C. for about 23 hours or until a constant weight was achieved.

XRPD and DSC analysis data confirmed that the product obtained was bosentan form 7.
Molar yield=0.83 g
Chemical purity>99% (measured by HPLC)
Polymorphic purity=high (measured by DSC)

Example 4

Method for Preparing Bosentan Form 7

A mixture of bosentan, cyclohexanone (2 vol) and ethanol (2 vol) was heated to about 80° C. to obtain a clear solution. This solution was cooled to about 30° C. within about 30 minutes and stirred at this temperature for 30 minutes. n-Hexane (15 vol) was then added to the cooled solution resulting in a solid precipitate. The suspension was further stirred for about 21 hours. The suspension was then filtered to obtain the desired crystalline solid and said solid was dried under vacuum at 25° C. for about 13 hours or until a constant weight was achieved.
XRPD and DSC analysis data confirmed that the product obtained was bosentan form 7.
Molar yield=0.54 g
Chemical purity>99% (measured by HPLC)
Polymorphic purity=high (measured by DSC)

Example 5

Method for Preparing Bosentan Form 8

A mixture of bosentan, ethyl acetoacetate (0.8 vol), octanol (2 vol) and n-pentyl acetate (1.2 vol) was heated to about 100° C. The resultant suspension was filtered at this temperature under vacuum. The filtrate was then cooled to about 26° C. within about 15 minutes, resulting in the formation of a solid precipitate, and stirred at that temperature for about 4 hours. The suspension was then filtered to obtain the desired crystalline solid and said solid was dried under vacuum at 25° C. for about 13 hours or until a constant weight was achieved.
XRPD and DSC analysis data confirmed that the product obtained was bosentan form 8.
Molar yield=0.42 g
Chemical purity>99% (measured by HPLC)
Polymorphic purity=high (measured by DSC)

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. Crystalline form 5 of bosentan characterized by an X-ray diffraction pattern comprising two or more peaks selected from peaks at 2θ values 4.02, 6.12, 8.38, 9.39, 10.04, 15.26, 17.72, 17.98, 18.81, 19.28, 20.31, 21.05, 27.57, 31.91 and 45.65±0.2° θ.

2. Crystalline form 5 of bosentan of claim 1 characterized by a DSC trace comprising endothermic peaks at about 93° C.±2° C. and about 196° C.±2° C.

3. Crystalline form 5 of bosentan of claim 1 having:
   (i) an XRPD trace substantially as shown in FIG. 1; or
   (ii) a DSC trace substantially as shown in FIG. 2; or
   (iii) a TGA trace substantially as shown in FIG. 3.

4. A process for preparing crystalline form 5 of bosentan according to claim 1, comprising the steps of:
   (a) dissolving bosentan in one or more organic solvent(s);
   (b) causing a crystalline solid to precipitate from the solution obtained in step (a); and
   (c) isolating the crystalline solid obtained from step (b), wherein the solvent in step (a) comprises ethyl acetoacetate.

5. A process according to claim 4, wherein:
   (i) the solvent is heated in step (a) until a clear solution is obtained; or
   (ii) the crystalline solid is precipitated in step (b) by cooling the solution; or
   (iii) the precipitated solid is isolated in step (c) by filtration; or
   (iv) the isolated solid from step (c) is dried under vacuum until a constant weight is achieved.

6. A process for preparing crystalline form 5 of bosentan according to claim 1, comprising the steps of:
   (a) heating bosentan in ethyl acetoacetate until a clear solution is obtained;
   (b) cooling the solution from step (a) until a precipitate forms; and
   (c) filtering the suspension from step (b) and drying the obtained solid under vacuum at about 20-40° C. until a constant weight is achieved.

7. Crystalline form 6 of bosentan characterized by an X-ray diffraction pattern comprising two or more peaks selected from peaks at 2θ values 3.87, 7.51, 8.84, 11.14, 18.74 and 23.30±0.2° θ.

8. Crystalline form 6 of bosentan of claim 7 characterized by a DSC trace comprising endothermic peaks at about 78° C.±2° C. and about 134° C.±2° C.

9. Crystalline form 6 of bosentan of claim 7 having:
   (i) an XRPD trace substantially as shown in FIG. 4; or
   (ii) a DSC trace substantially as shown in FIG. 5; or
   (iii) a TGA trace substantially as shown in FIG. 6.

10. A process for preparing crystalline form 6 of bosentan according to claim 7, comprising the steps of:
    (a) dissolving bosentan in one or more organic solvent(s) and optionally water;
    (b) causing a crystalline solid to precipitate from the solution obtained in step (a); and
    (c) isolating the crystalline solid obtained from step (b).

11. A process according to claim 10, wherein:
    (i) the solvent, each solvent or one or more of the solvent(s) in step (a) is a $C_1$-$C_6$ alcohol; or
    (ii) bosentan is dissolved in step (a) by heating in butan-2-ol and amyl alcohol and adding water; or
    (iii) the solid is precipitated in step (b) by cooling the solution from step (a) and adding cyclohexane; or
    (iv) the precipitated solid from step (b) is isolated by filtration; or
    (v) the isolated solid from step (c) is dried under vacuum until a constant weight is achieved.

12. A process for preparing crystalline form 6 of bosentan according to claim 7, comprising the steps of:
    (a) dissolving or suspending bosentan in a solvent system comprising one or more $C_1$-$C_6$ alcohol(s);
    (b) adding water to the solution or suspension from step (a) until a clear solution is obtained;
    (c) cooling the solution from step (b) to between about 20-40° C.;
    (d) adding cyclohexane to the solution from step (c) until a precipitate is formed; and (e) filtering the resultant precipitated solid and drying under vacuum at between about 20-30° C. until a constant weight is achieved.

13. A process according to claim 12, wherein:
   (i) the solvent system in step (a) comprises butan-2-ol and amyl alcohol; or
   (ii) the solvents are heated in step (a) to about 80° C.

14. Crystalline form 7 of bosentan characterized by an X-ray diffraction pattern comprising two or more peaks selected from peaks at 2θ values 3.64, 4.23, 4.95, 7.04, 7.68, 8.23, 9.05, 9.66, 10.48, 13.95, 15.20, 16.17, 17.37, 18.06, 20.03, 22.13 and 23.62±0.2° θ.

15. Crystalline form 7 of bosentan of claim 14 characterized by a DSC trace comprising endothermic peaks at about 75° C.±2° C. and about 130° C.±2° C.

16. Crystalline form 7 of bosentan having:
   (i) an XRPD trace substantially as shown in FIG. 7; or
   (ii) a DSC trace substantially as shown in FIG. 8; or
   (iii) a TGA trace substantially as shown in FIG. 9.

17. A process for preparing crystalline form 7 of bosentan according to claim 14, comprising the steps of:
   (a) dissolving bosentan in one or more organic solvent(s);
   (b) causing a crystalline solid to precipitate from the solution obtained in step (a); and
   (c) isolating the crystalline solid obtained from step (b).

18. A process according to claim 17, wherein:
   (i) bosentan is dissolved in step (a) in the or each solvent until a clear solution is obtained; or
   (ii) bosentan is dissolved in step (a) by heating the or each solvent; or
   (iii) the solvent, each solvent or one or more of the solvent(s) in step (a) is a $C_1$-$C_6$ alcohol; or
   (iv) the solvents in step (a) are a mixture of cyclohexanone and n-butanol or a mixture of cyclohexanone and ethanol; or
   (v) the crystalline solid is precipitated by adding n-hexane to the solution from step (a); or
   (vi) the solid is isolated in step (c) by filtration; or
   (vii) the isolated solid from step (c) is dried under vacuum until a constant weight is achieved.

19. A process for preparing crystalline form 7 of bosentan according to claim 14, comprising the steps of:
   (a) dissolving bosentan in a mixture of cyclohexanone and a $C_1$-$C_6$ alcohol;
   (b) cooling the solution from step (a) to about 30° C. within about 30 minutes whilst stirring;
   (c) adding n-hexane to the solution from step (b) to form a precipitate and stirring the suspension for about 2-5 hours; and
   (d) filtering the suspension from step (c) and drying the obtained solid under vacuum at about 20-40° C. until a constant weight is achieved.

20. A process according to claim 19, wherein:
   (i) the $C_1$-$C_6$ alcohol in step (a) is n-butanol; or
   (ii) bosentan is dissolved in step (a) by heating the mixture until a clear solution is obtained.

21. A process for preparing crystalline form 7 of bosentan according to claim 14, comprising the steps of:
   (a) dissolving bosentan in a mixture of cyclohexanone and a $C_1$-$C_6$ alcohol;
   (b) cooling the solution from step (a) to about 30° C. within about 30 minutes whilst stirring;
   (c) adding n-hexane to the solution from step (b) to form a precipitate and stirring the suspension for between about 15-25 hours; and
   (d) filtering the suspension from step (c) and drying the obtained solid under vacuum at about 20-40° C. until a constant weight is achieved.

22. A process according to claim 21, wherein:
   (i) the $C_1$-$C_6$ alcohol in step (a) is ethanol; or
   (ii) bosentan is dissolved in step (a) by heating the mixture until a clear solution is obtained.

23. A method of treating hypertension, ischemia, vasospasm, angina pectoris, and pulmonary arterial hypertension comprising administering a therapeutically effective amount of bosentan crystalline form 5 as claimed in claim 1 to a subject in need thereof.

24. A method of treating hypertension, ischemia, vasospasm, angina pectoris, and pulmonary arterial hypertension comprising administering a therapeutically effective amount of bosentan crystalline form 6 as claimed in claim 7 to a subject in need thereof.

25. A method of treating hypertension, ischemia, vasospasm, angina pectoris, and pulmonary arterial hypertension comprising administering a therapeutically effective amount of bosentan crystalline form 7 as claimed in claim 14 to a subject in need thereof.

26. A pharmaceutical composition comprising crystalline form 5 of bosentan according to claim 1, and one or more pharmaceutically acceptable excipients.

27. A pharmaceutical composition comprising crystalline form 6 of bosentan according to claim 7, and one or more pharmaceutically acceptable excipients.

28. A pharmaceutical composition comprising crystalline form 7 of bosentan according to claim 14, and one or more pharmaceutically acceptable excipients.

* * * * *